(12) United States Patent
Cheng

(10) Patent No.: US 8,240,311 B2
(45) Date of Patent: Aug. 14, 2012

(54) 3D VENTILATION DEVICE FOR SEPARATING BODY SKIN FROM CLOTHES

(76) Inventor: Tsan-Hsiung Cheng, Tainan County (TW)

(*) Notice: Subject to any disclaimer, the term of this patent is extended or adjusted under 35 U.S.C. 154(b) by 918 days.

(21) Appl. No.: 12/329,674

(22) Filed: Dec. 8, 2008

(65) Prior Publication Data

US 2010/0139665 A1    Jun. 10, 2010

(51) Int. Cl.
  *A61F 13/00* (2006.01)
  *A61F 5/24* (2006.01)
  *A61F 5/28* (2006.01)
  *A61F 6/04* (2006.01)
  *A61F 5/37* (2006.01)
  *A61F 13/15* (2006.01)
  *A61G 15/00* (2006.01)
  *A61L 15/00* (2006.01)
  *A42C 5/04* (2006.01)
  *A42C 5/02* (2006.01)
  *A42B 1/20* (2006.01)

(52) U.S. Cl. ...... 128/846; 128/96.1; 128/99.1; 128/844; 128/845; 128/883; 2/182.3; 2/182.8; 2/209.3; 2/209.5; 2/209.7; 602/60; 602/61; 602/67; 602/70; 602/72; 602/73; 602/75; 604/392; 604/396; 604/400

(58) Field of Classification Search .......... 128/844–846, 128/883, 96.1, 99.1; 2/182.3, 182.8, 209.3, 2/209.5, 209.7; 602/60, 61, 67, 70, 72, 73, 602/75; 604/392, 396, 400
See application file for complete search history.

(56) References Cited

U.S. PATENT DOCUMENTS 5,819,318 A * 10/1998 Tse ................................ 2/182.1
* cited by examiner

*Primary Examiner* — Patricia Bianco
*Assistant Examiner* — Nihir Patel
(74) *Attorney, Agent, or Firm* — Muncy, Geissler, Olds & Lowe, PLLC

(57) ABSTRACT

The present invention is related to a 3D ventilation device for separating body skin from clothes including an elastic meshed fabric, an elastic framework and a fixing device, wherein the 3D elastic framework which supports and holds the elastic meshed fabric, is fixed by the fixing device to locate between the skin and the clothes, so as to form a ventilative chamber for achieving the separation. Here, the elastic framework can be bent to adapt to different body shapes or portions and adjusted to provide most comfortable wearing angle, so that a proper air flowing can be achieved between the skin or the body portion and the clothes, thereby keeping the skin dry.

6 Claims, 7 Drawing Sheets

3D VENTILATION DEVICE FOR SEPARATING BODY SKIN FROM CLOTHES

FIELD OF THE INVENTION

The present invention is related to a three-dimensional elastic framework, which can form a space between cloth and skin for allowing ventilation and heat dispersing.

BACKGROUND OF THE INVENTION

Generally, a cover or cloth located on the skin for allowing ventilation and heat dispersing is mainly focused on separating the affected part from the underclothes.

Take the cover for separating the affected part as an example. A swab or breathable cotton is always used to cover on the affected part. However, when the user washes his/her hand or sweats, the swab or breathable cotton might absorb water or sweat easily which actually provides a great environment for bacteria proliferation and causes a secondary affection. Besides, when the cover absorbs water, it becomes non-breathable, so that it is difficult for the affected part to stay dry, and even, the new grown tissue might be stuck by the cover which will destroy the tissue as exchanging the cover, and of course, extend the recovering period.

Moreover, modern people often wear adjustable underwear or clothes capable of modifying body shape which always tightly constricts the skin, so that it is very easily to become muggy and wet. Therefore, this kind of clothes always utilizes special knitting manner or introduces thereinto a material with high thermal conductivity for achieving greater ventilation or heat dispersing capability.

When utilizing the specific knitting method for increasing ventilation, such as, by track and column braiding and lattice braiding, the increased spaces for ventilation are only the intervals among lines which are extremely small and only located on the surface of textile fabrics, and even the liner material is selected to be breathable or meshed, the skin, the liner material and the outer cloth still keep close together, so that the discomfort caused from muggy and sweat still exist.

When introducing materials with high thermal conductivity into knitting, only the body temperature can be dispersed, and since human body achieves heat dispersing mainly through sweating, if it can not provide sufficient space for ventilation, the feeling of muggy still can not be effectively reduced.

Therefore, no matter the cover placed on the affected part or the clothes worn on the skin, after a long time attachment to the skin, it might easily cause a humid and muggy environment which actually encourages the growth of bacteria and fungi, so as to further influence health and sanitation.

SUMMARY OF THE INVENTION

Skin is the outermost protection for organisms and the basic principle for taking care of skin is to keep the skin dry and breathing freely, especially for the injured skin, like cuts or wounds. However, the modern people chase for perfect body shape through wearing adjustable skin-tight clothes and disregard of ventilation. Therefore, the present invention provides a 3D ventilation device for separating the skin from the clothes, so as to maintain the ventilation space therebetween, thereby reducing the burden on the skin.

The present invention is related to a 3D ventilation device for separating body skin from clothes, in which the separation is achieved by a 3D elastic framework, which can be made of elastic hard polymer or bent metal lines covered by soft material such as cloth or sponge, so as to provide supportability and also adaptation to different body shapes or body portions, thereby it can be adjusted to most comfortable wearing angle. The elastic framework can form a separated space for propping up the clothes so as to provide the air flowing space between the skin or body portion and the clothes and thus to keep the skin dry.

When the present invention is applied to daily life, through the elastic framework covering the skin or organ and propping up the clothes to provide great ventilation, the uncomfortable muggy feeling can be reduced, so as to eliminate the causes of skin diseases, such as high temperature and sweat humidity. Especially for woman's breast and man's testicle which are always covered by tight underwear, the present invention can prevent a direct contact between the organ and the clothes, so as to reduce the burden on the skin and rubbings against the clothes and also increase the buffer of compression.

Besides, when the present invention is applied to medical purposes, through the elastic framework covering around the affected part and the interior lines of the elastic framework propping up the clothes, it can prevent the affected part from rubbing against the clothes or sticking on contaminants which might cause inflammation and infection. And, owing to the separated space, the external medicine can be fixed or great ventilation can be provided without contacting the affected part, and further, the clothes will not be stained or will not influence the new grown tissue, thereby facilitating the recovery.

BRIEF DESCRIPTION OF THE DRAWINGS

The foregoing aspects and many of the attendant advantages of this invention will be more readily appreciated as the same becomes better understood by reference to the following detailed description, when taken in conjunction with the accompanying drawings, wherein.

DESCRIPTION OF THE PREFERRED EMBODIMENT

Figure 1:
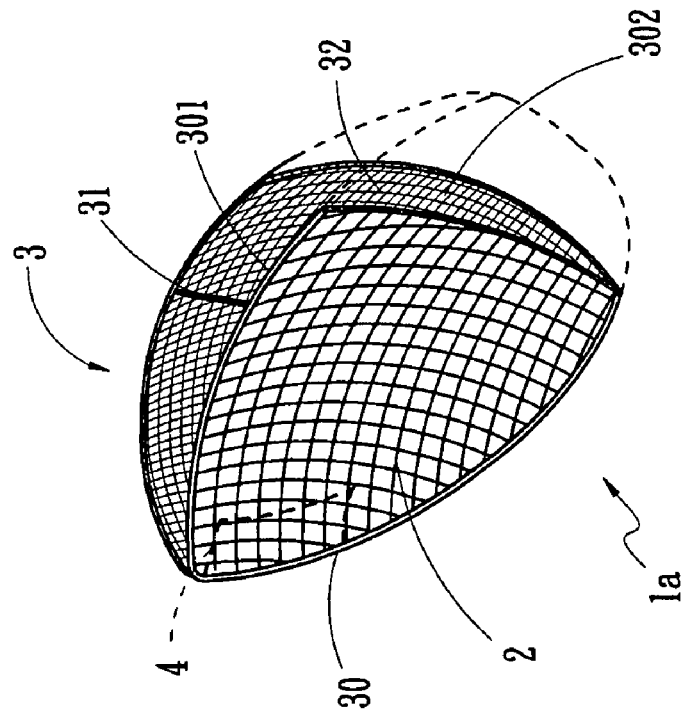
FIG. 1 is a three-dimensional drawing showing the present invention according to a first preferred embodiment.
Figure 2:
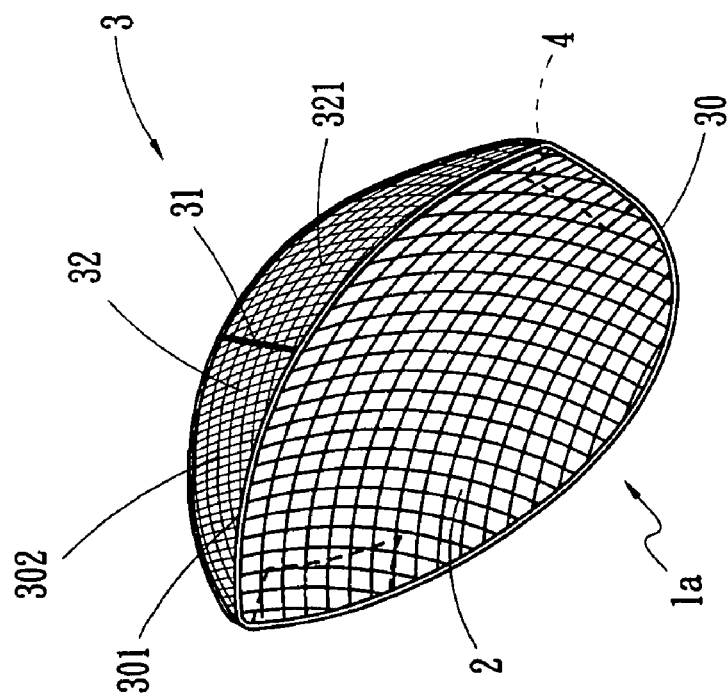
FIG. 2 is a three-dimensional sectional view showing the present invention.

The present invention provides a 3D ventilation device for separating body skin from the cloth. As shown in FIG. 1, the 3D ventilation device 1a includes an elastic meshed fabric 2, an elastic framework 3 and a fixing device 4, wherein:

The elastic meshed fabric 2 is a spaced-knitted meshed fabric for providing proper air flow.

The elastic framework 3 has a 3D structure with elasticity which can be made of elastic hard polymer or bent metal lines covered by soft material such as cloth or sponge. The elastic framework 3 includes a frame 30 and interior lines 31, wherein the frame 30 provides the supporting tension for the elastic framework 3, and the whole 3D structure of the elastic framework 3 is formed by the combination of the frame 30 and the interior lines 31. A 3D hollow chamber 32 with an opening 321 is formed inside the elastic framework 3, and the chamber 32 is used to provide the ventilative space. Besides, the frame 30 of the elastic framework 3 is covered by the propped elastic meshed fabric 2 so as to provide a soft and comfortable contact with the skin through the 3D ventilation device 1a.

The fixing device 4 is connected with the elastic framework 3, for tying or fixing the 3D ventilation device 1a.

Figure 3:
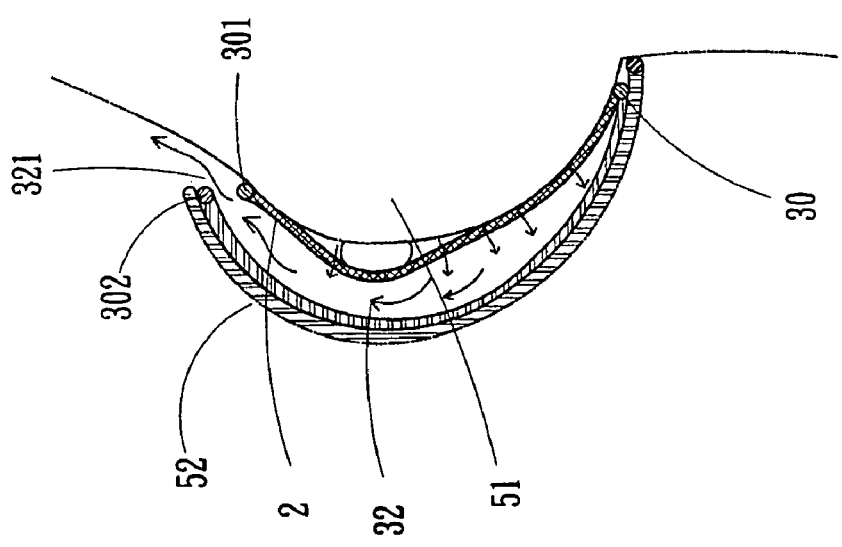
FIG. 3 is a schematic view showing the air flowing route as the present invention is used on woman's breast.
Figure 7:
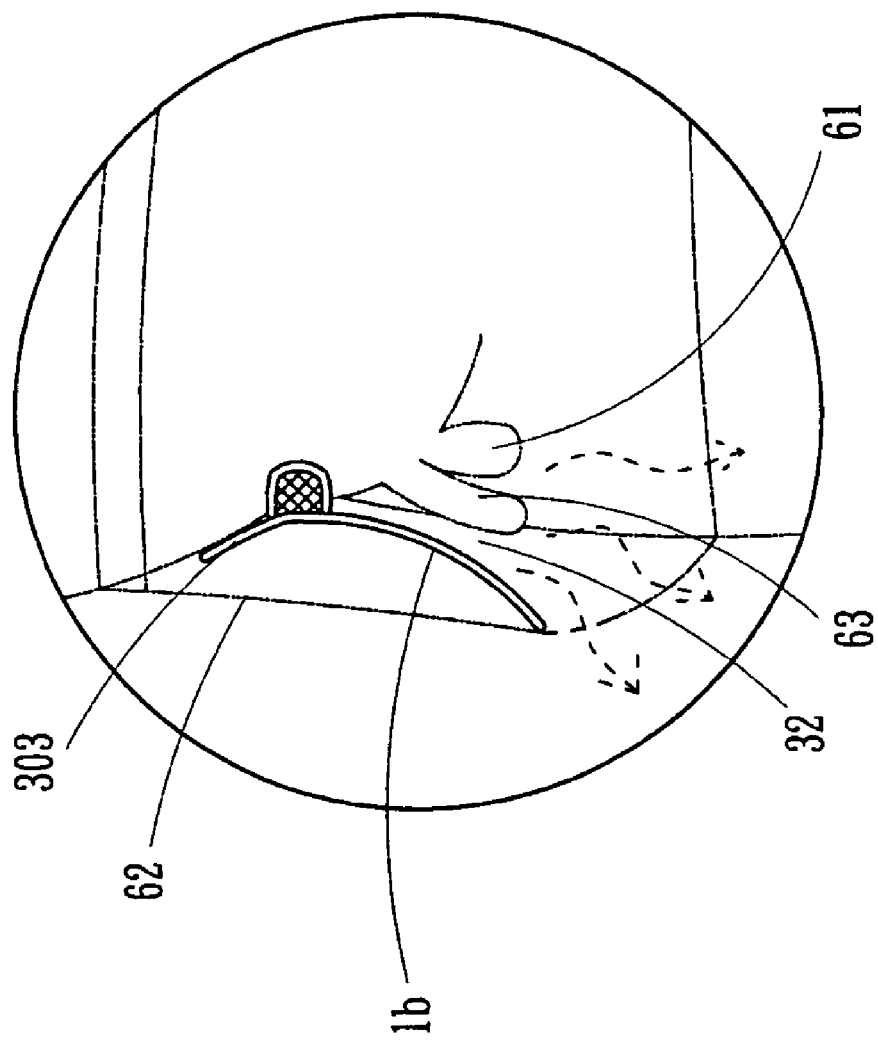
FIG. 7 a schematic view showing the air flowing route as the present invention is used on man's testicle.
Figure 11:
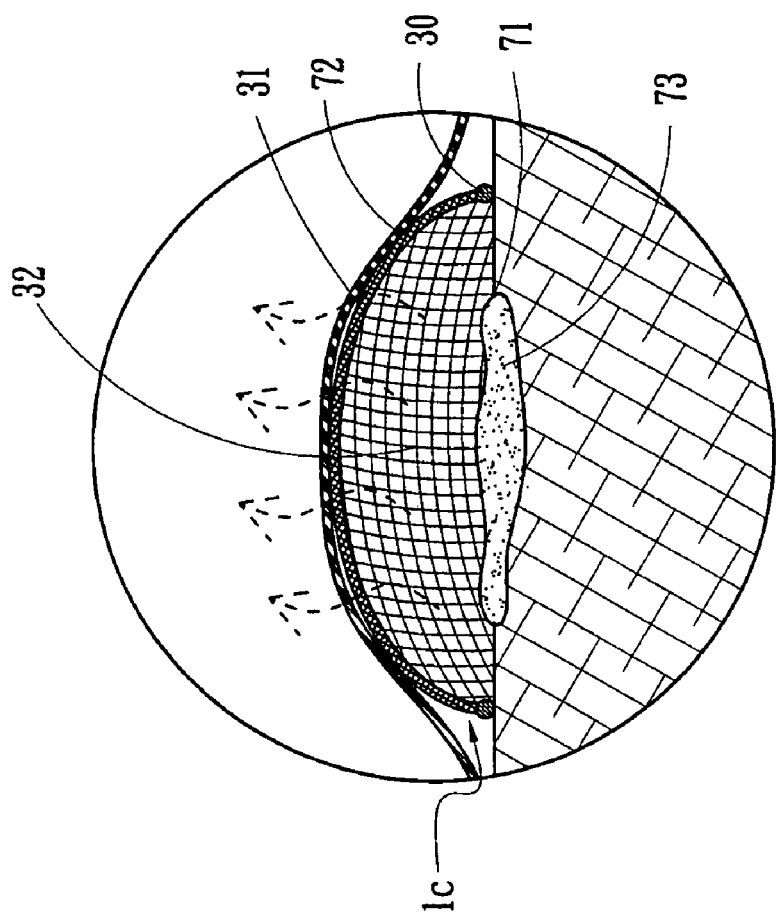
FIG. 11 is a schematic view showing the air flowing route as the present invention is used to cover the affected part.
Figure 10:
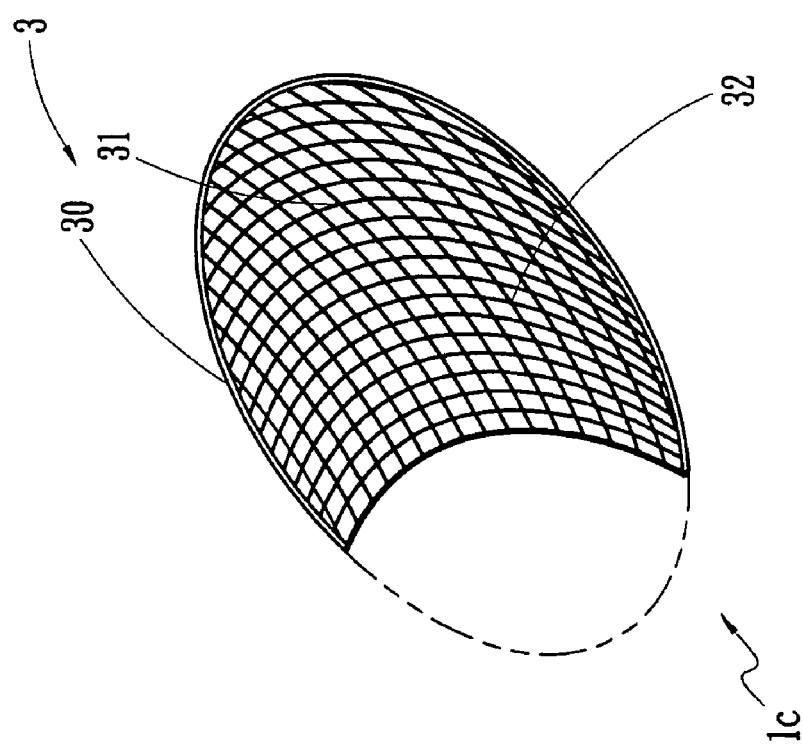
FIG. 10 is a three-dimensional sectional view showing the present invention as being used for covering an affected part according to a third preferred embodiment.
Figure 13:
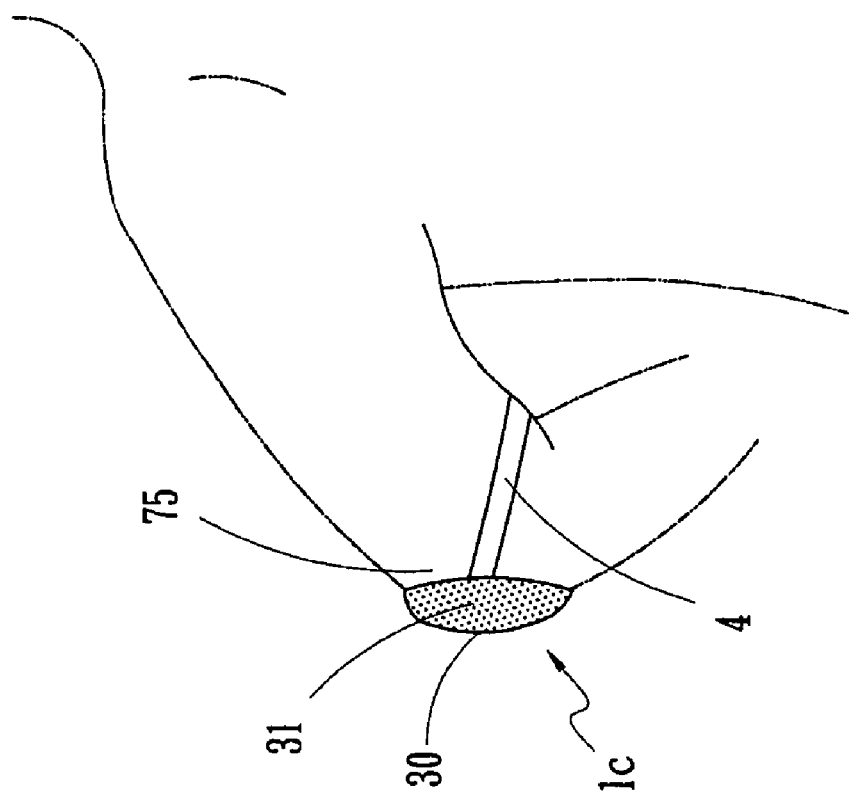
FIG. 13 is a schematic view showing the wearing situation as the affected part is located on a bendable skin surface.
Figure 12:
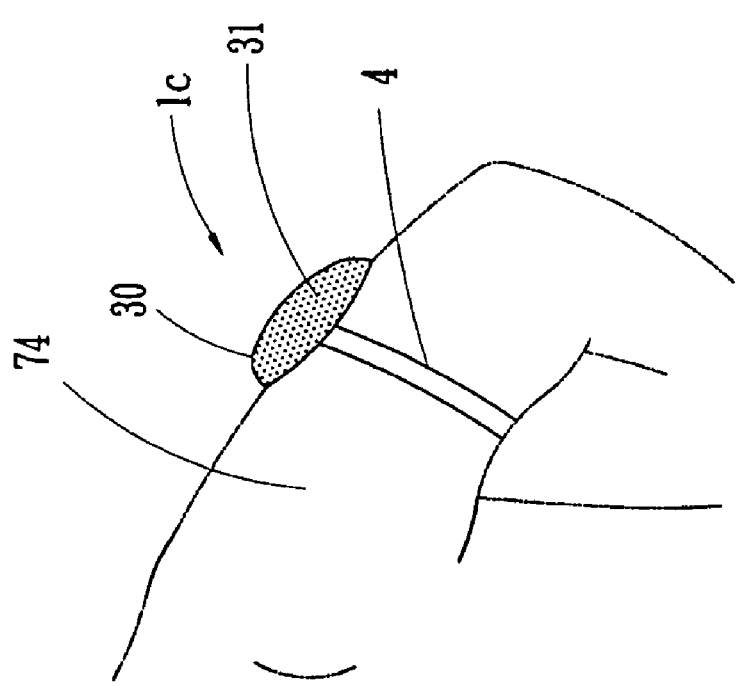
FIG. 12 is a schematic view showing the wearing situation as the affected part is located on an unbent skin surface.

The applying examples for the present invention are respectively shown in FIG. 3, FIG. 7 and FIG. 11. The present invention is mainly used to separate the sensitive part of human body from the clothes and/or prevent from the muggy and wet situation therebetween. For example, the 3D ventilation device 1a can be located between the breast 51 and the brassiere 52, the 3D ventilation device 1b can be located between the testicle 61 and the underpants 62, and the 3D ventilation device 1c can be located between the affected part 71 and the clothes 72, which are respectively described below.

Please refer to FIG. 1, FIG. 2, FIG. 3 and FIG. 4. The 3D ventilation device 1a of the present invention is applied to provide buffer, protection and ventilation for woman's breast 51. Here, the elastic framework 3 is formed to be a double-layered 3D bowl shape and have an inner framework 301 and an outer framework 302. The inner and outer frameworks 301, 302 both hold a curved surface, and the curved surface held by the inner framework 301 is smaller than that held by the outer framework 302, so that between the inner and the outer frameworks 301, 302, a separated hollow chamber 32 is formed. Furthermore, the elastic meshed fabric 2 is fixed on and held by the frame of the elastic framework 3, so that the heat produced from the skin can be outputted through the opening 321 of the hollow chamber 32, thereby dispersing heat and keeping dry. Besides, the fixing device 4 which will not damage the cloth is connected to the outer edge of the outer framework 302 of the elastic framework 3. Here, the fixing device 4 can be connected by Velcro, button and sewing, or can be tightly located between the lower edge and inwardly concave portion of the brassiere 52 and the breast 51, without influencing the appearance and function of the brassiere 52.

Figure 4:
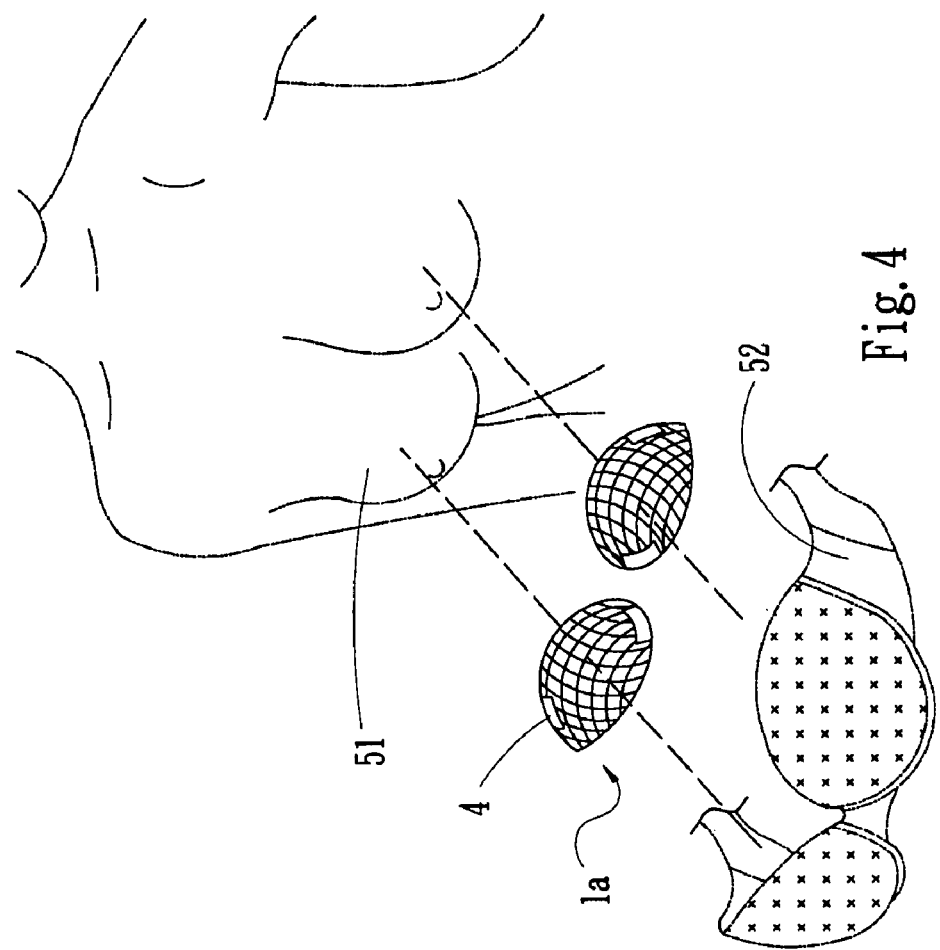
FIG. 4 is a schematic view showing the wearing situation as the present invention is used on woman's breast.

As shown in FIG. 3 and FIG. 4, the 3D ventilation device 1a is placed at the inner side of the brassiere 52 first, and then, both are worn on. Here, the elastic meshed fabric 2 on the inner framework 301 can support the breast 51, and the outer framework 302 can contact with the brassiere 52 and fix the position of the 3D ventilation device 1a. Therefore, the chamber 32 formed between the inner framework 301 and the outer framework 302 can facilitate the exhaust of heat and sweat, thereby achieving the effects of ventilation and heat dispersing.

Figure 5:
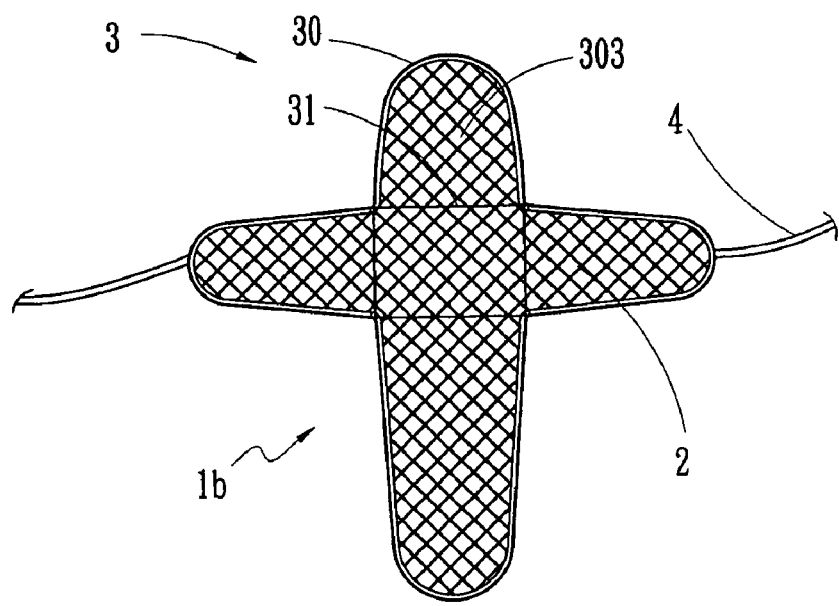
FIG. 5 is schematic view showing the structure of the present invention for being used on man's testicle according to a second preferred embodiment.
Figure 6:
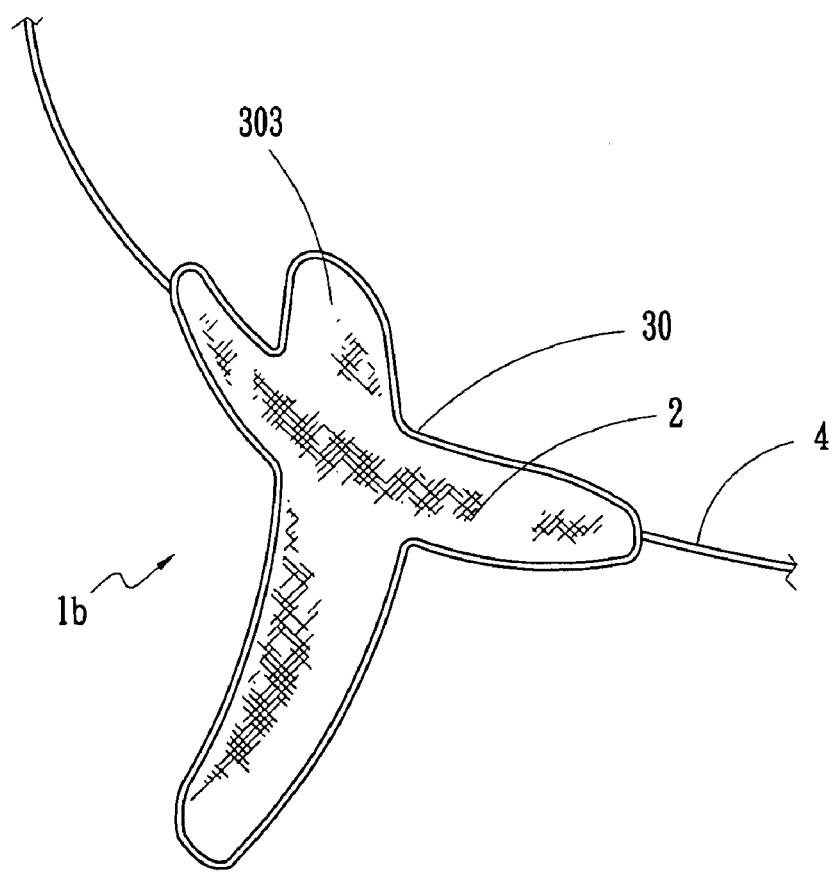
FIG. 6 is a three-dimensional drawing showing the present invention which is used on man's testicle.

Please further refer to FIG. 5, FIG. 6 and FIG. 7 which show a second preferred embodiment of the present invention, wherein the 3D ventilation device 1b is used to provide protection, ventilation and heat dispersing for man's testicle 61. Here, the frame 30 of the elastic framework 3 is formed to have a cross shape, wherein the central portion of the cross shape is supported by plural interior lines 31, and the upper portion of the cross shape is a protruded fixing piece 303 for preventing the 3D ventilation device 1b from being lifted up owing to the body movement. Moreover, the elastic meshed fabric 2 is held by the frame 30 of the elastic framework 3 to form a cross surface, and two ends of the elastic framework 3 are respectively connected with the fixing device 4, which can be elastic tape or elastic belt.

Figure 8:
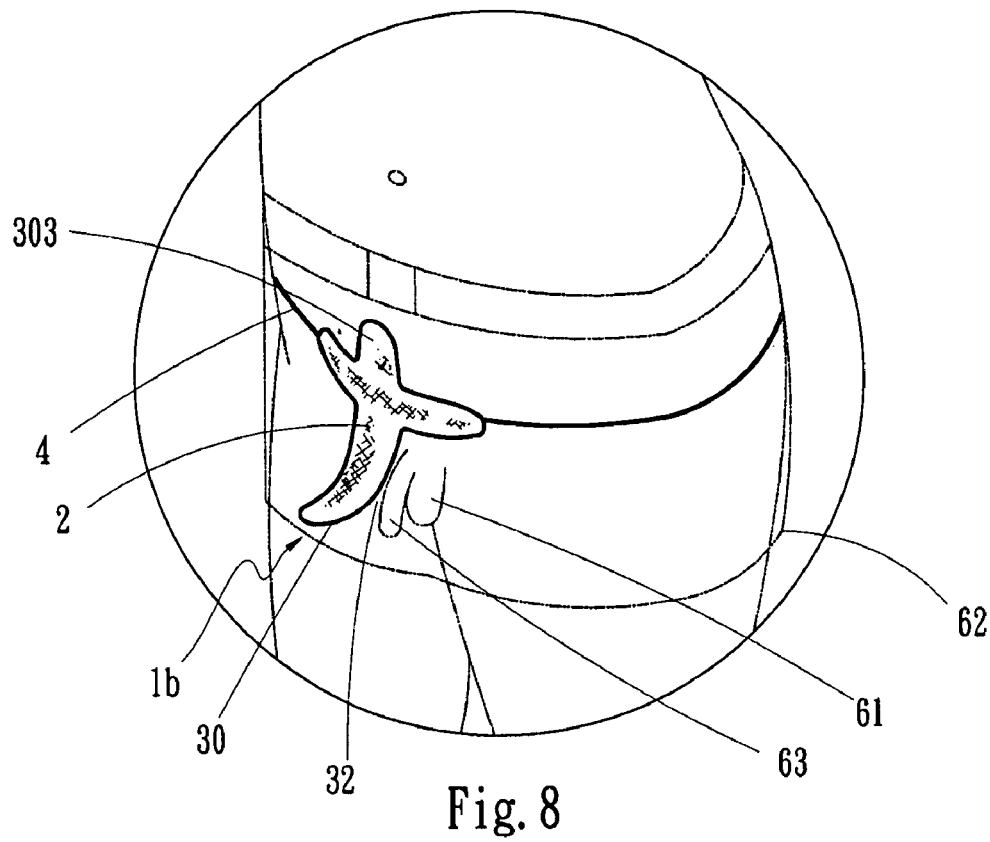
FIG. 8 is a schematic view showing the first kind of wearing situation as the present invention is used on man's testicle.
Figure 9:
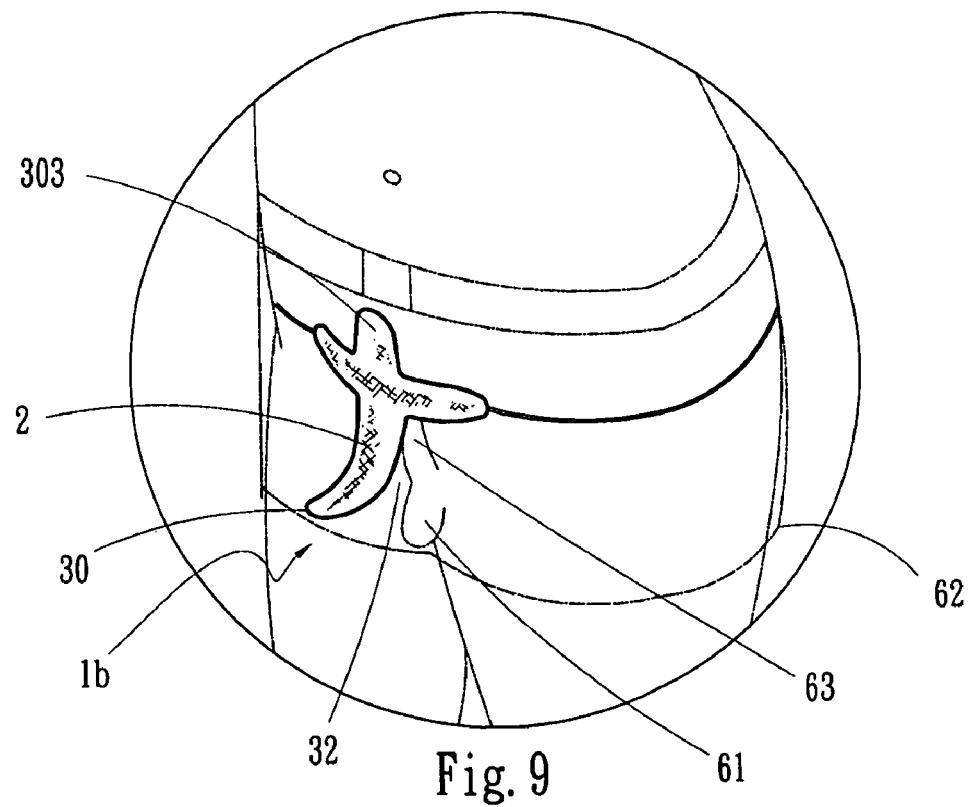
FIG. 9 is a schematic view showing the second first kind of wearing situation as the present invention is used on man's testicle.

As shown in FIG. 7, FIG. 8 and FIG. 9, first, the 3D ventilation device 1b is placed and fixed on the hip through the fixing device 4 and then the underpants 62 is put on, so that the 3D ventilation device 1b is located between the testicle 61 and the underpants 62. Here, the user can freely adjust the angle of the elastic framework 3 for adapting to the body shape, and the lower edge of the frame 30 of the elastic framework 3 can be bent upwardly for propping up the underpants 62, which originally stays close to the testicle 61, so as to form the chamber 32 for allowing ventilation and the free moving of the penis 63. Besides, it also can be the penis 63 is moved upward and supported by the elastic meshed fabric 2, so as to increase the circulation space in the chamber 32, thereby achieving an even better ventilation and heat dispersing effect. Then, when calling the nature, since the fixing device 4 is an elastic belt, the 3D ventilation device 1b can be easily moved away and back without inconvenience.

Please refer to FIG. 10, FIG. 11, FIG. 12 and FIG. 13, which show a third preferred embodiment of the present invention for medical purposes. The frame 30 of the elastic framework 3 of the 3D ventilation device 1c is covered on the skin around the affected part 71, and the interior lines 31 are interwoven with each other to form a supportable spaced-knitted meshed surface, so as to form the hollow chamber 32 inside the 3D ventilation device 1c for separating the affected part from the clothes 72. Furthermore, the fixing device 4 is connected to two sides of the 3D ventilation device 1c for fixing thereof on the limb 74 or the joint 75 aside the affected part 71. Here, the fixing device 4 can be elastic tape or elastic belt. Therefore, the 3D ventilation device 1c can avoid the affected part 71 or the dressing 73 from rubbing against the clothes 72, so that the affected part 71 can easily stay uncontaminated and keep dry for facilitating recovery.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A 3D ventilation device for separating body skin from clothes, comprising:
    an elastic meshed fabric;
    an elastic framework, including a frame, which is used to fix the edge of the elastic meshed fabric, and interior lines, which are connected with the frame for forming a three-dimensional structure, wherein through the bent elastic framework, clothes are propped up against an outside surface of the elastic framework to form a chamber for ventilation, and a protruded fixing piece is located at the upper end of the elastic framework for preventing the 3D ventilation device from being lifted up;

a fixing device, connected to two ends of the elastic framework for fixing the 3D ventilation device.

2. The 3D ventilation device as claimed in claim 1, wherein the elastic meshed fabric is a spaced-knitted meshed surface with multiple holes.

3. The 3D ventilation device as claimed in claim 1, wherein the elastic framework is made of elastic hard polymer covered by soft material.

4. The 3D ventilation device as claimed in claim 3, wherein the elastic hard polymer can be made by metal lines.

5. The 3D ventilation device as claimed in claim 3, wherein the soft material is cloth or sponge.

6. The 3D ventilation device as claimed in claim 1, wherein the frame and the interior lines of the elastic framework are bendable for adapting to the shapes and curves of body and limbs.

* * * * *